United States Patent
Kimura et al.

(10) Patent No.: US 10,246,675 B2
(45) Date of Patent: Apr. 2, 2019

(54) BIOCHEMICAL CARTRIDGE, AND BIOCHEMICAL CARTRIDGE AND CARTRIDGE HOLDER SET

(71) Applicant: HITACHI HIGH-TECHNOLOGIES CORPORATION, Tokyo (JP)

(72) Inventors: Ryusuke Kimura, Tokyo (JP); Hiromi Yamashita, Tokyo (JP); Motohiro Yamazaki, Tokyo (JP); Taro Nakazawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 122 days.

(21) Appl. No.: 14/762,301

(22) PCT Filed: Jan. 27, 2014

(86) PCT No.: PCT/JP2014/051611
§ 371 (c)(1),
(2) Date: Jul. 21, 2015

(87) PCT Pub. No.: WO2014/119497
PCT Pub. Date: Aug. 7, 2014

(65) Prior Publication Data
US 2015/0361387 A1 Dec. 17, 2015

(30) Foreign Application Priority Data
Jan. 31, 2013 (JP) .................................. 2013-016328

(51) Int. Cl.
*C12M 3/00* (2006.01)
*F16K 31/126* (2006.01)
(Continued)

(52) U.S. Cl.
CPC .......... *C12M 23/42* (2013.01); *B01L 3/50273* (2013.01); *B01L 3/502738* (2013.01);
(Continued)

(58) Field of Classification Search
CPC .. B01L 3/50273; F16K 31/126; F16K 31/145; F16K 31/165
See application file for complete search history.

(56) References Cited

U.S. PATENT DOCUMENTS 7,766,033 B2 * 8/2010 Mathies .............. F16K 99/0001
137/297
2004/0209354 A1 * 10/2004 Mathies ..................... B01F 5/10
435/287.2

(Continued)

FOREIGN PATENT DOCUMENTS

EP 1867733 A1 12/2007
EP 2 479 466 A1 7/2012
(Continued)

OTHER PUBLICATIONS

Extended European Search Report received in corresponding European Application No. 14746499.4 dated Aug. 24, 2016.
International Search Report of PCT/JP2014/051611.

*Primary Examiner* — Matthew D Krcha
(74) *Attorney, Agent, or Firm* — Mattingly & Malur, PC

(57) ABSTRACT

A cartridge sealed from ambient air is used to send a liquid without causing the liquid to contact the fluid inside the cartridge. Inside of the cartridge 1 sealed from ambient air are provided chambers that send and receive reagents, and an elastic body membrane 51 is attached to the bottom surface. The cartridge main body 51 does not have a groove or anything else that becomes a channel, and the membrane 51 is not bonded to portions that become channels. A channel, not formed in a normal state, is formed upon deforming the membrane 51 under air pressure in the unbonded portion, and the fluid is moved inside. A valve function is provided at an inlet of each chamber, and the fluid is internally moved in any direction with channel deformation.

6 Claims, 11 Drawing Sheets

(51) Int. Cl.
- *F16K 7/17* (2006.01)
- *G01N 35/08* (2006.01)
- *B01L 3/00* (2006.01)
- *C12M 1/40* (2006.01)
- *C12M 1/107* (2006.01)

(52) U.S. Cl.
CPC ............ *C12M 21/18* (2013.01); *C12M 23/36* (2013.01); *F16K 7/17* (2013.01); *F16K 31/126* (2013.01); *G01N 35/08* (2013.01); *B01L 2300/0816* (2013.01); *B01L 2300/0874* (2013.01); *B01L 2300/123* (2013.01); *B01L 2400/0481* (2013.01); *B01L 2400/0655* (2013.01)

(56) References Cited

U.S. PATENT DOCUMENTS

| | | | |
|---|---|---|---|
| 2006/0076068 A1 | 4/2006 | Young et al. | |
| 2007/0166200 A1* | 7/2007 | Zhou | B01L 3/5025 422/400 |
| 2010/0216193 A1 | 8/2010 | Gomi et al. | |
| 2011/0315227 A1 | 12/2011 | Shu | |
| 2012/0266986 A1 | 10/2012 | Wimberger-Friedl et al. | |
| 2013/0130262 A1* | 5/2013 | Battrell | B01L 3/50273 435/6.12 |

FOREIGN PATENT DOCUMENTS

| | | |
|---|---|---|
| GB | 2 453 310 A | 4/2009 |
| JP | 63-315956 A | 12/1988 |
| JP | 2006-234590 A | 9/2006 |
| JP | 2007-330179 A | 12/2007 |
| JP | 2011-030522 A | 2/2011 |
| WO | 2007/064635 A1 | 6/2007 |
| WO | 2009/054473 A1 | 4/2009 |
| WO | 2010/073020 A1 | 7/2010 |
| WO | 2011/048521 A1 | 4/2011 |

\* cited by examiner

[FIG. 1]
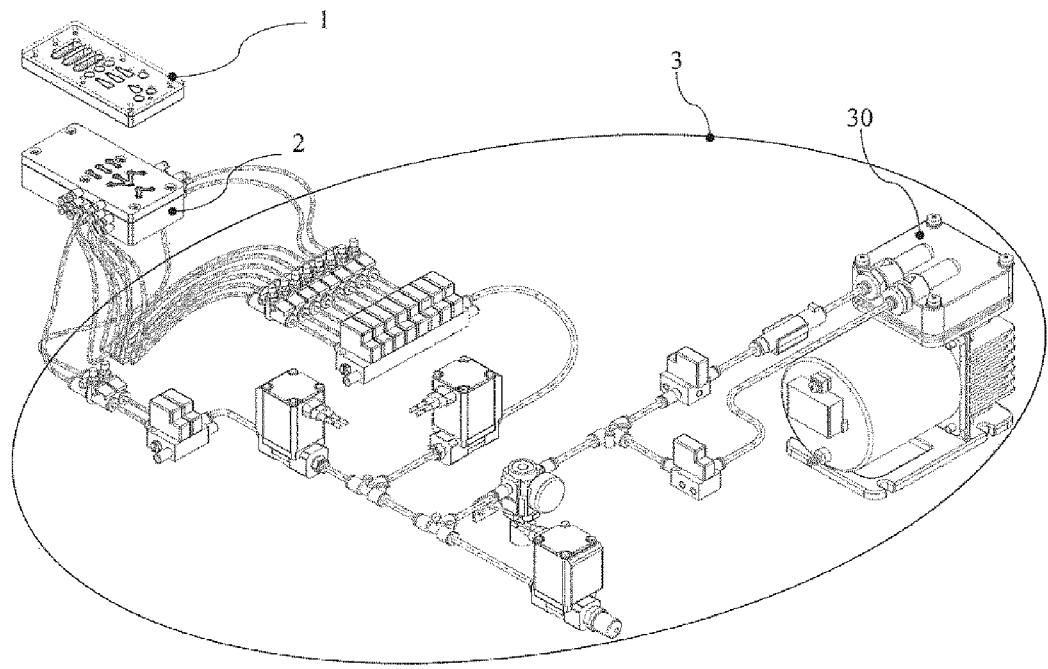
[FIG. 2]
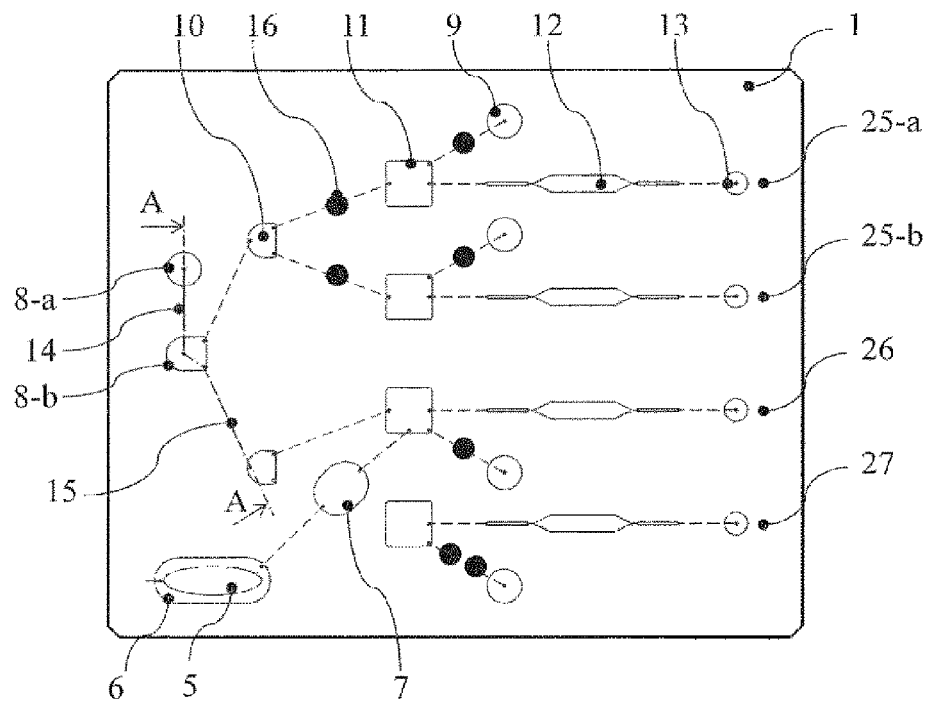

[FIG. 3]
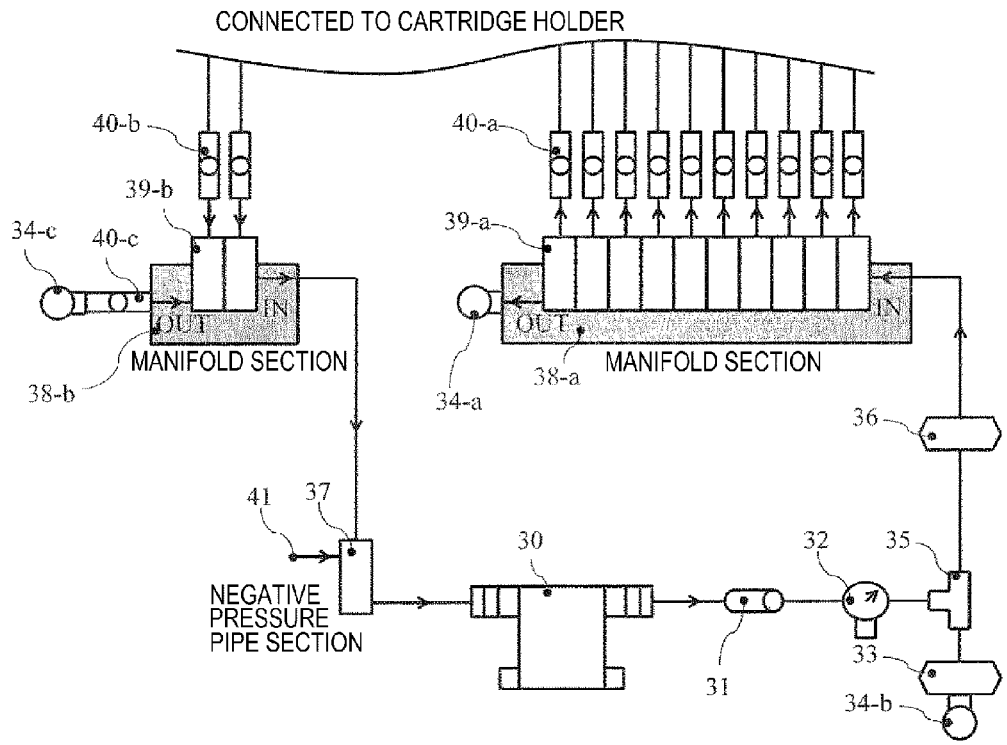
[FIG. 4]
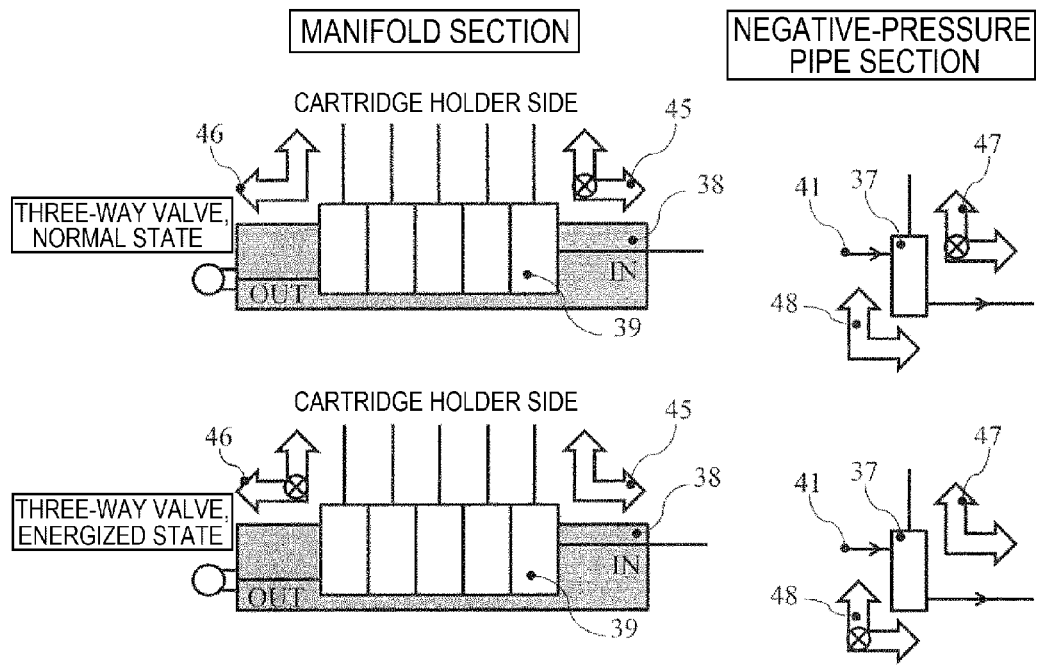

[FIG. 5]
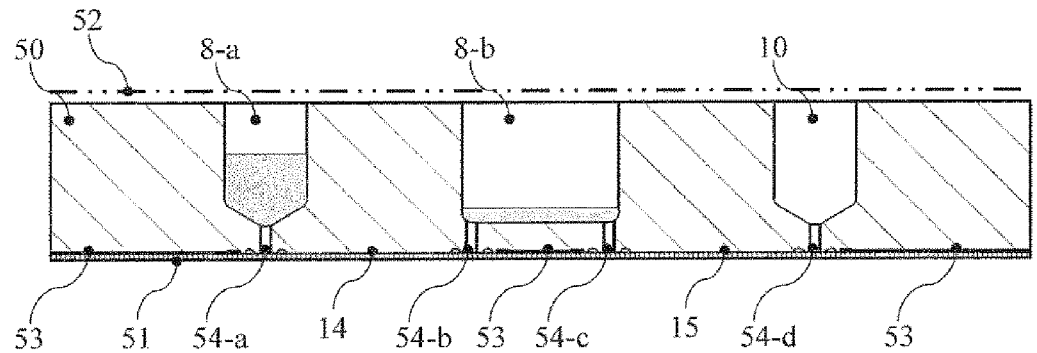
[FIG. 6]
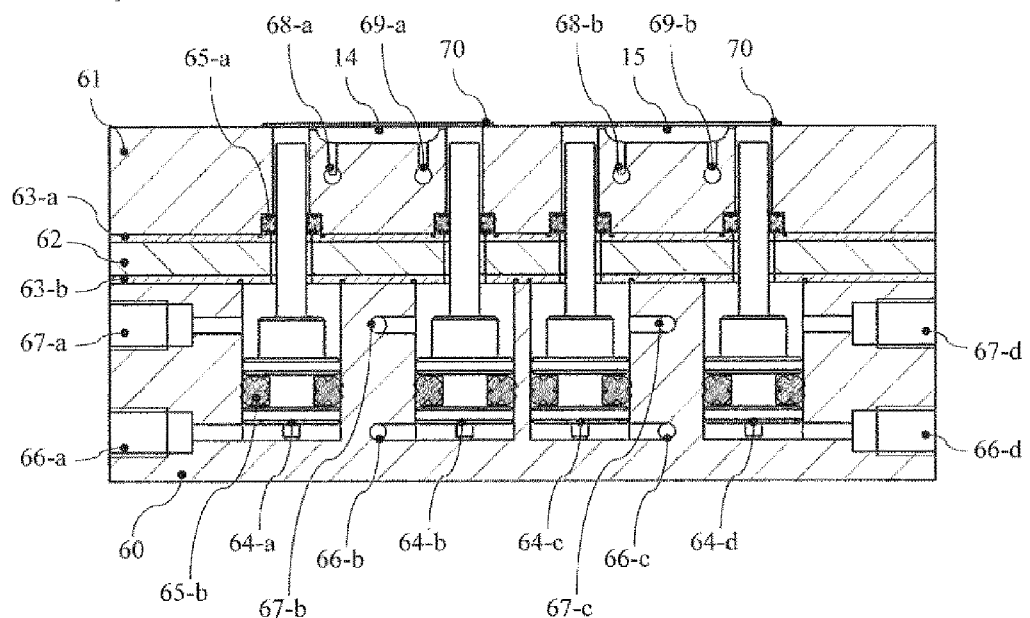

[FIG. 7]
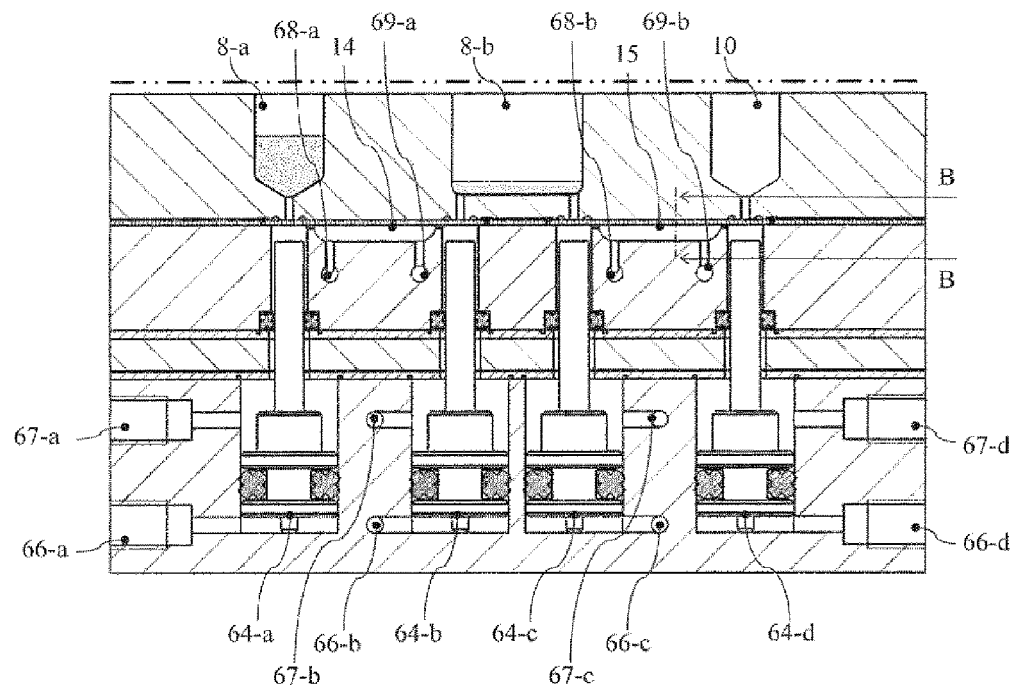
[FIG. 8]
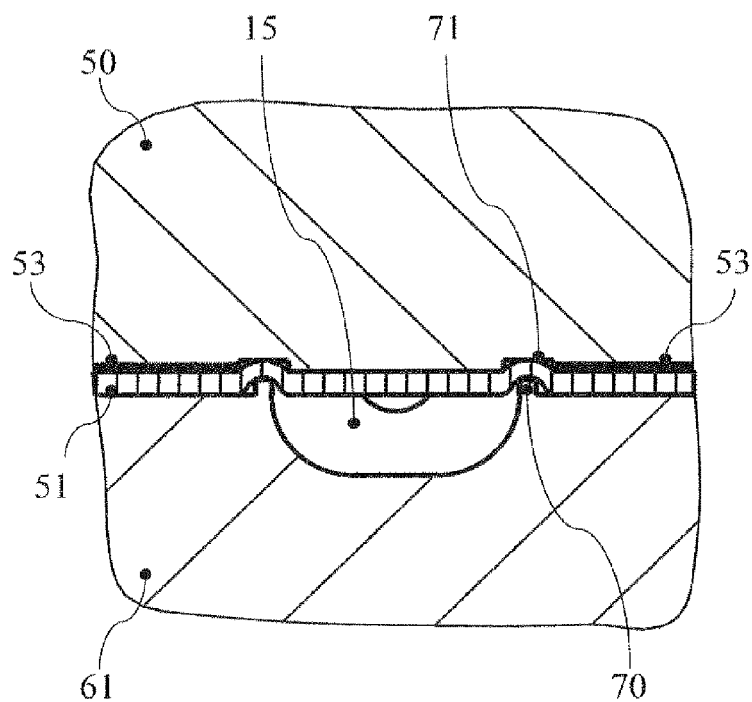

[FIG. 9]
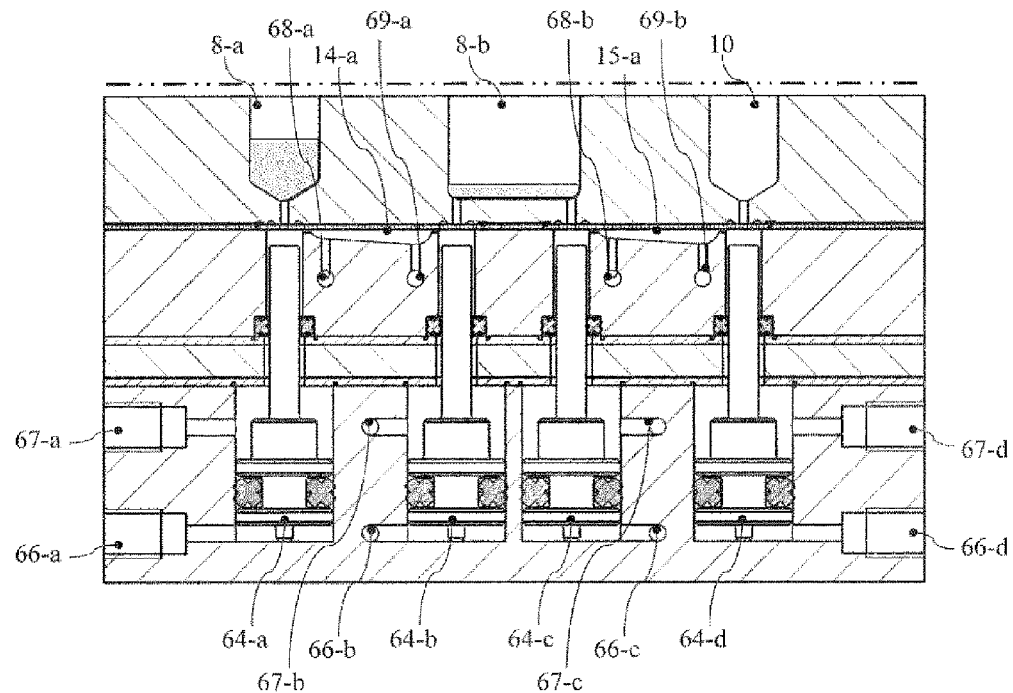
[FIG. 10]
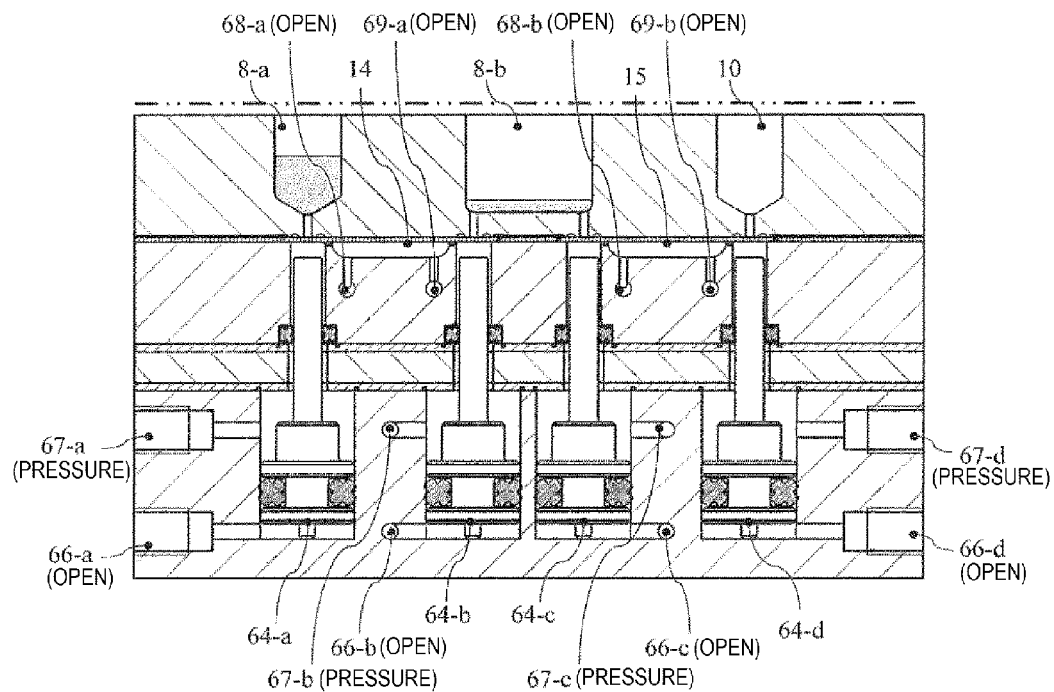

[FIG. 11]
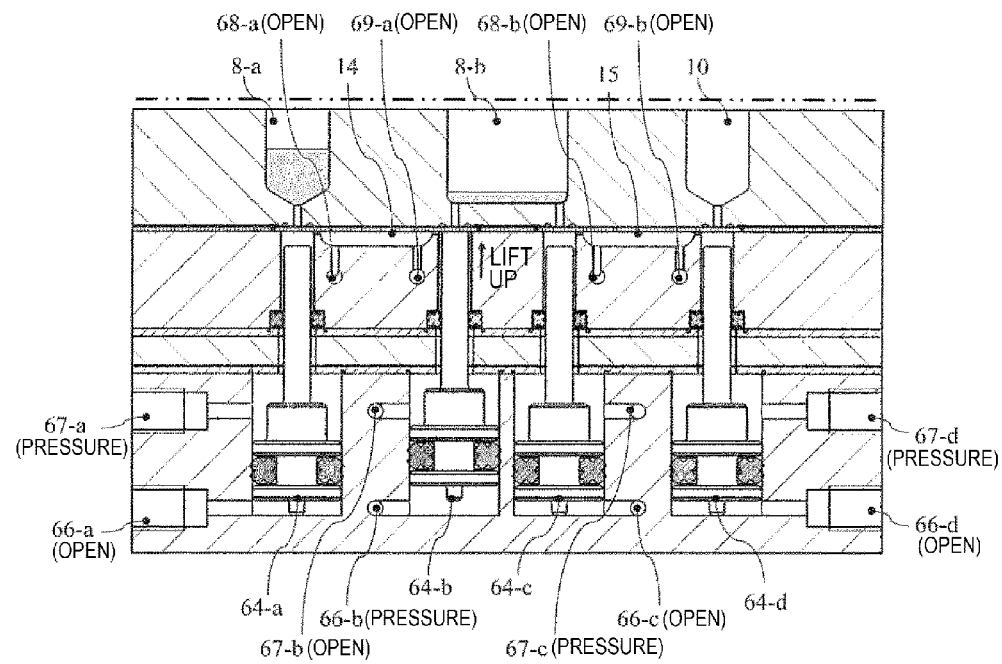
[FIG. 12]
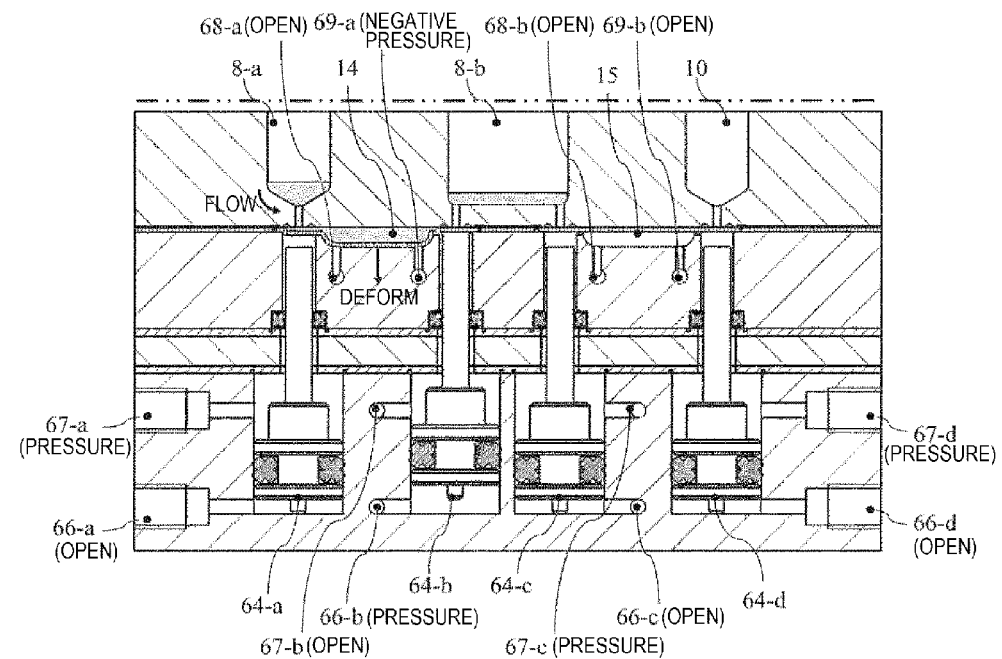

[FIG. 13]
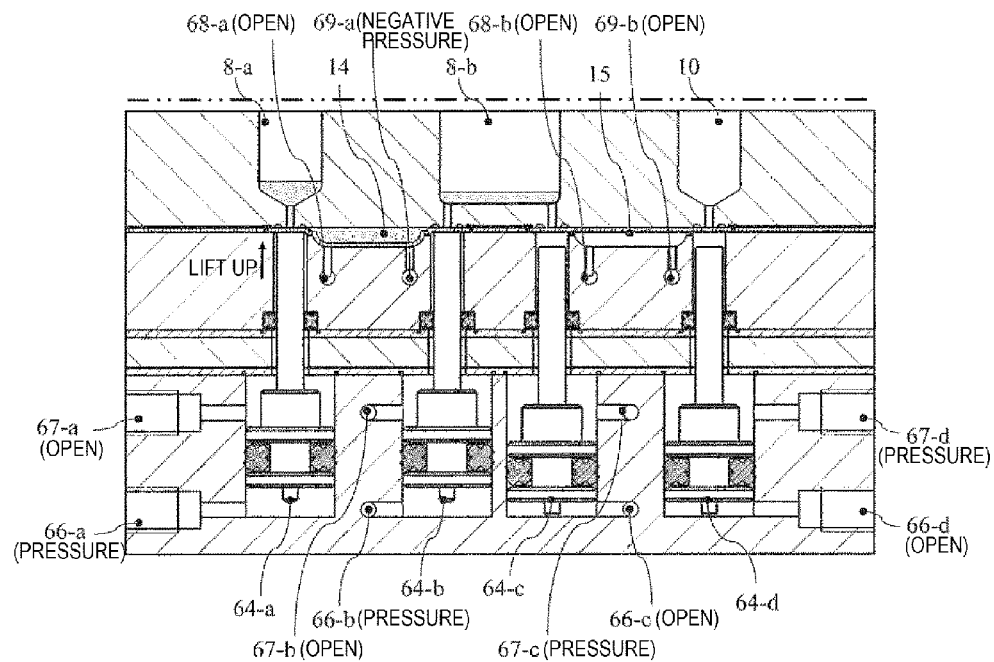
[FIG. 14]
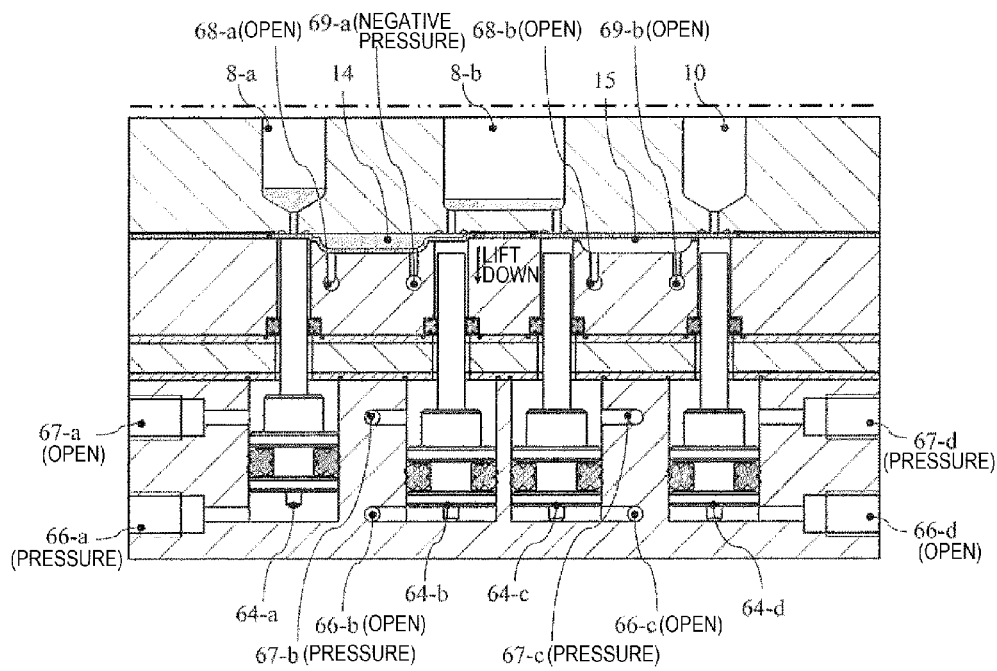

[FIG. 15]
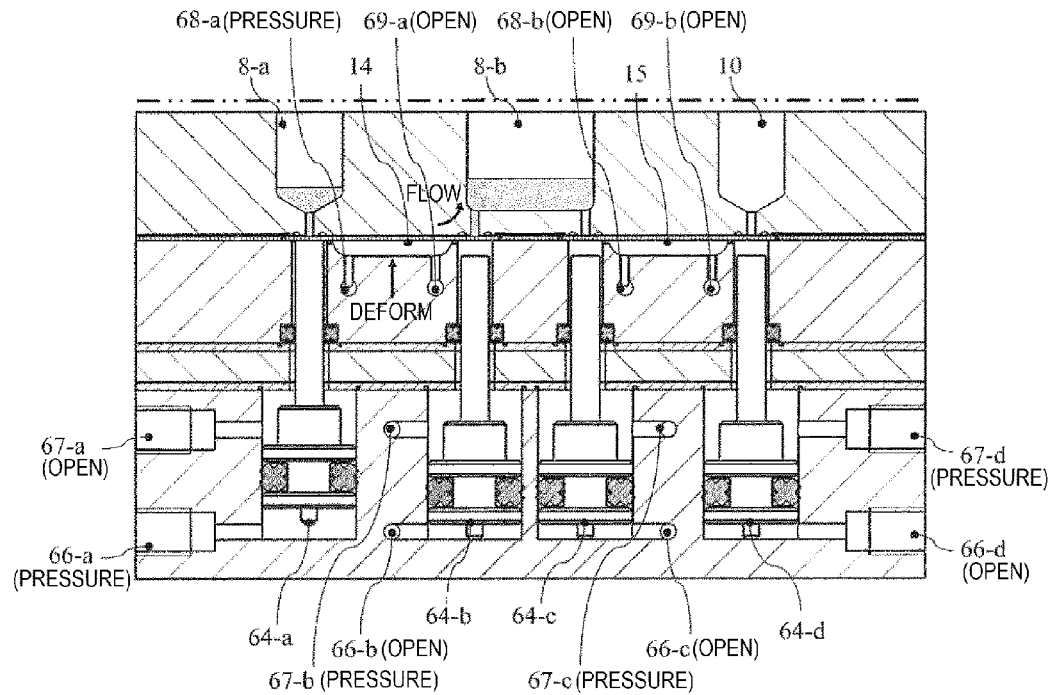
[FIG. 16]
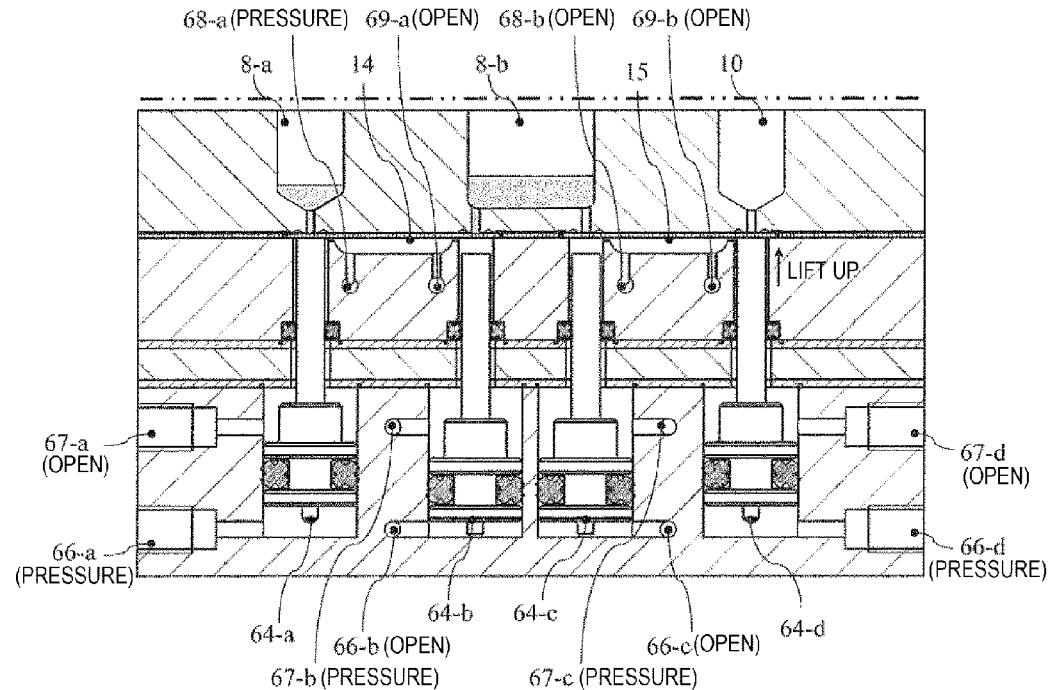

[FIG. 17]
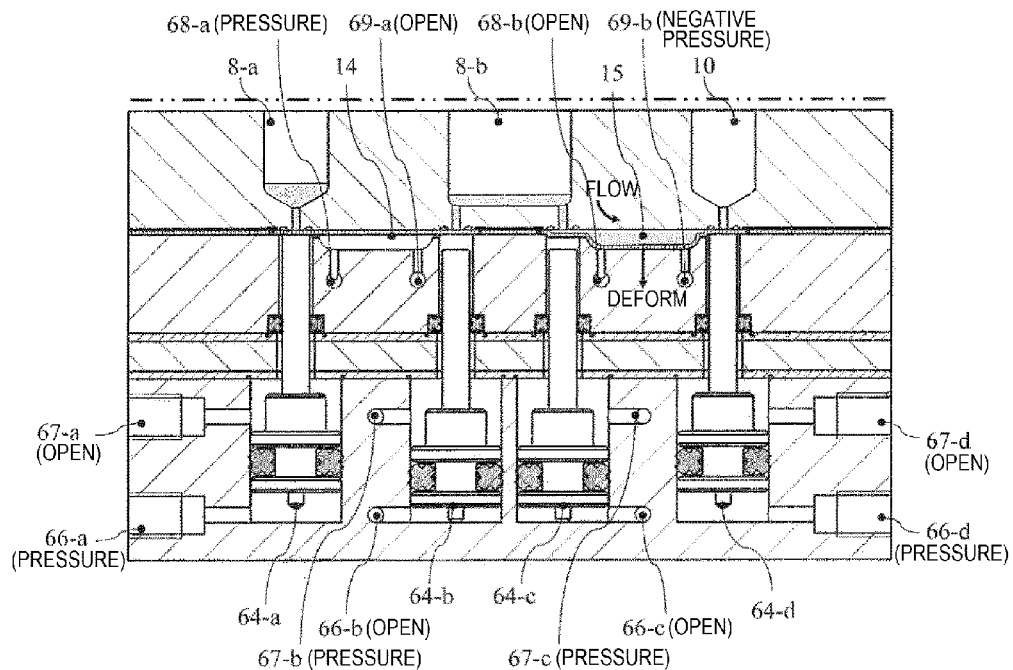
[FIG. 18]
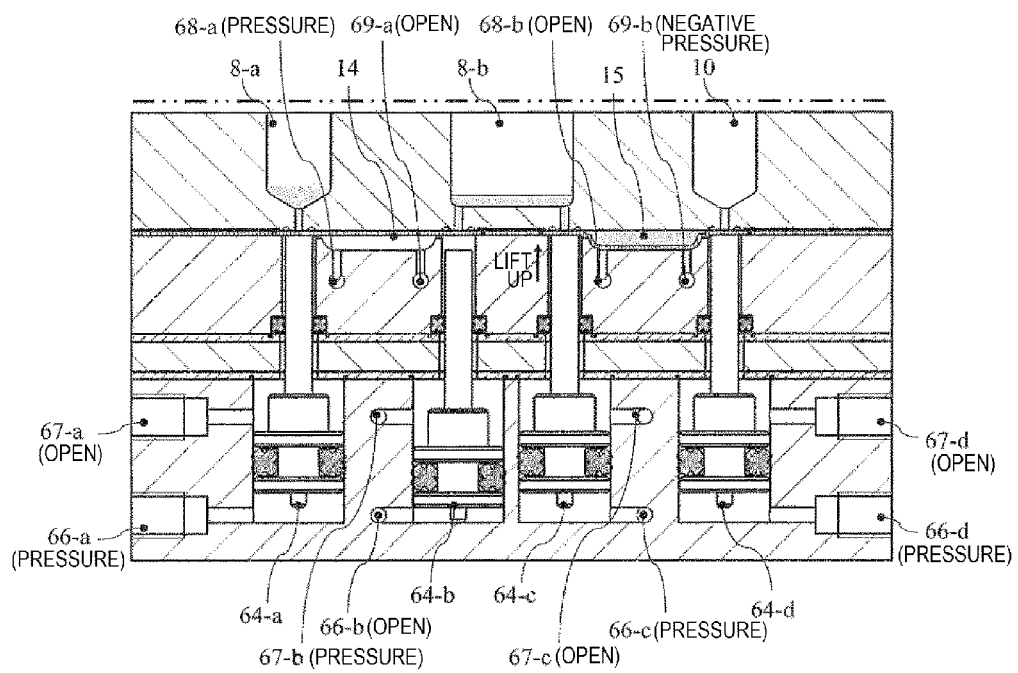

[FIG. 19]
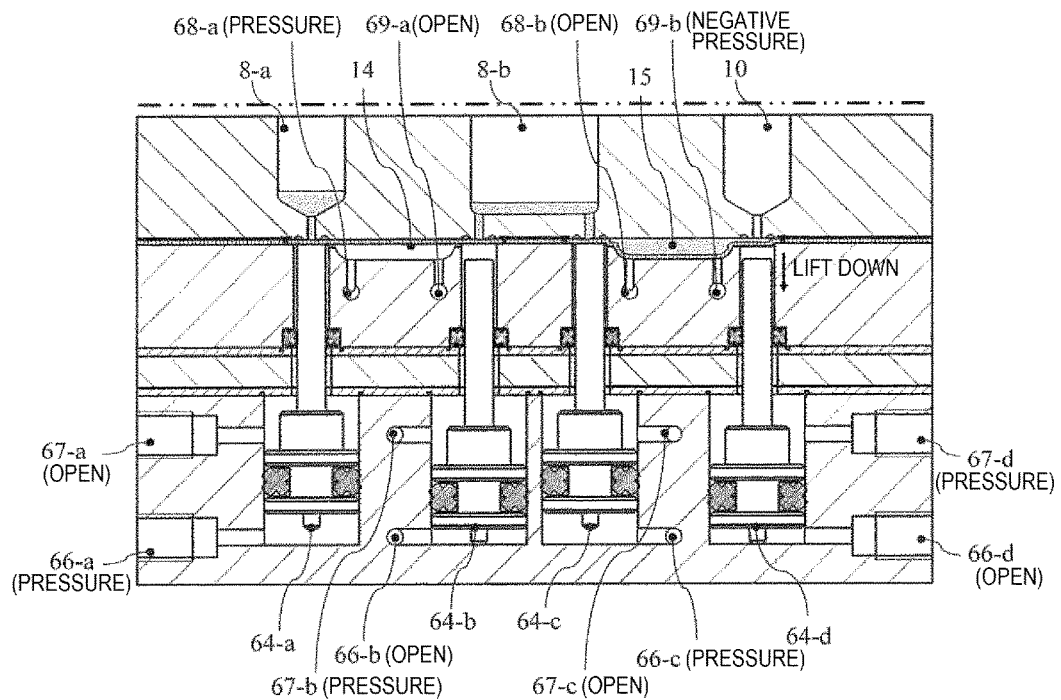
[FIG. 20]
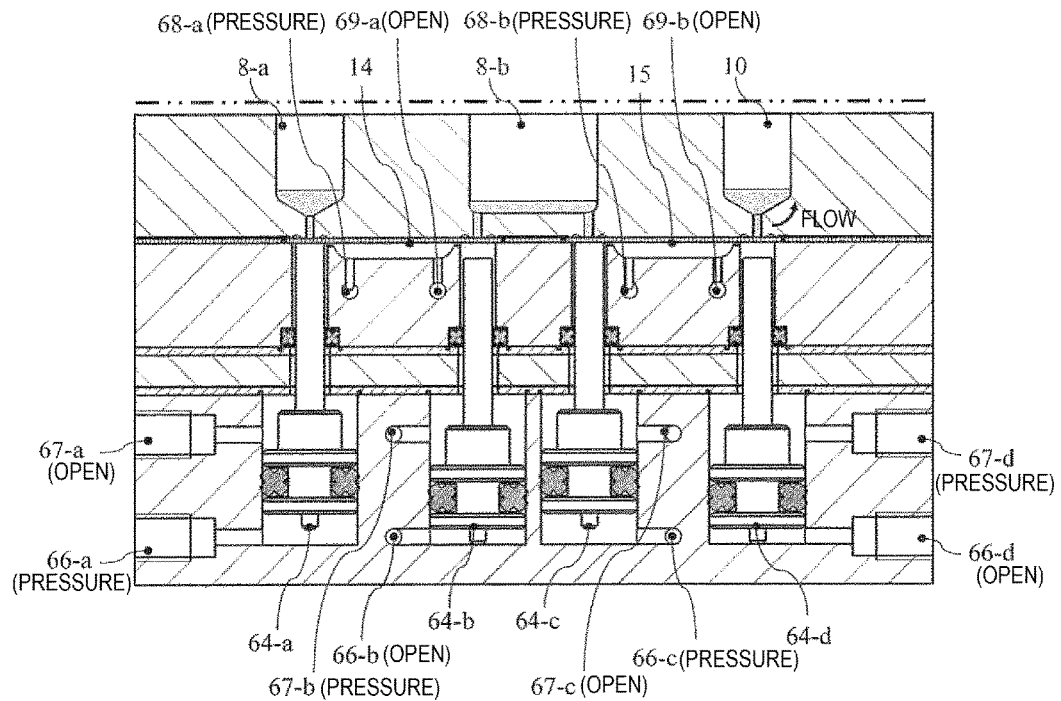

[FIG. 21]
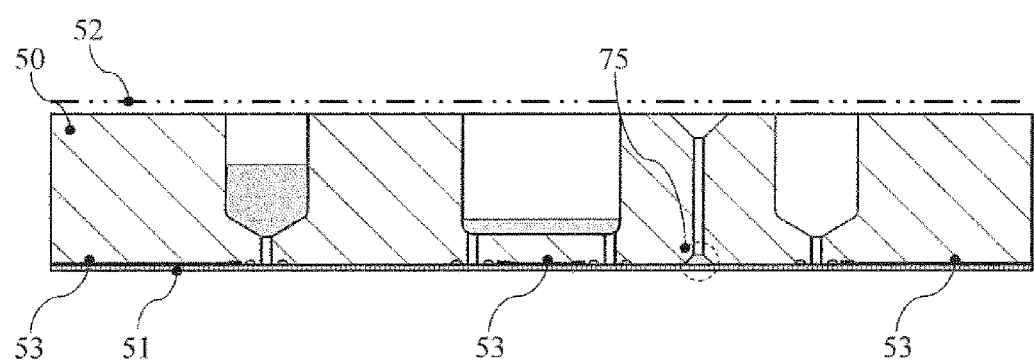

BIOCHEMICAL CARTRIDGE, AND BIOCHEMICAL CARTRIDGE AND CARTRIDGE HOLDER SET

TECHNICAL FIELD

The present invention relates to a biochemical cartridge, and a biochemical cartridge and cartridge holder set used to extract biological materials through biochemical reaction, and synthesize the materials as required for analysis.

BACKGROUND ART

Gene analysis, for example, requires performing various biochemical processes and reactions for samples (also called analytes or specimens) obtained from living organisms and other sources, such as in extraction and amplification of nucleic acids such as DNA and RNA. Such processes and reactions require accurately mixing several reagents with the sample. In performing biochemical processes by supplying reagents to the sample, the reagents need to be delivered to cells intended for different processes.

A method that is commonly used to mix reagents is a pipetting technique that uses a dispenser robot in an auto-analysis device and other applications, as described in Patent Literature 1. The dispenser robot is a unit that works by two- or three-dimensionally driving a dispensing mechanism over a certain range of the device to automatically draw in and out liquid through a nozzle or a tip attached to the end of the dispensing mechanism.

On the other hand, PCR (Polymerase Chain Reaction) is used to amplify DNA in the field of gene analysis. For gene analysis, a template DNA needs to be PCR amplified to levels that can be detected by a detector, and PCR is known to be very effective for gene analysis.

Handling of DNA and RNA requires care not to mix the target DNA and RNA with other DNA and RNA (hereinafter, such mixing will be referred to as "contamination"). PCR involves the risk of using a trace amount of DNA (a single molecule of DNA) as a template for amplification. Contamination by other DNA, particularly PCR amplified DNA fragments (PCR products) and low-molecular clone DNA thus needs to be prevented so that these will not be used as templates. This requires performing a PCR on a clean bench by following procedures in which a chamber for handling the target DNA such as in extraction is separately provided from a chamber used for PCR, and in which a sample is transported via a sample-containing tube to prevent entry of suspended DNA in air.

The pipetting technique using a dispenser robot described in Patent Literature 1 prevents contamination by washing the nozzle or using disposable tips. However, because the nozzles and tips travel in air, it is very difficult to prevent contamination by suspended DNA in air. Patent Literature 1 attempts to minimize the possibility of contamination by performing the procedures on a clean bench with chambers separately provided for handling of DNA and PCR.

There have been studies of processes that perform extraction, purification, amplification, and analysis of biological materials in series by causing a sample to react with reagents inside a micro space using a microdevice. A microdevice has a wide range of applications, including gene analysis. Using a microdevice offers many advantages, including less consumption of samples and reagents compared to common devices, improved portability as compared to setting various reagents, and disposability. Further, because a reaction is completed within a sealed space inside a small device, microdevices are considered desirable in dealing with the contamination problem. An example of microdevice application is disclosed in Patent Literature 2, which proposes a DNA extraction technique that uses a pre-treated chip.

CITATION LIST

Patent Literature

Patent Literature 1: JP-A-63-315956
Patent Literature 2: JP-A-2007-330179

SUMMARY OF INVENTION

Technical Problem

Quantitative control of fluids such as reagents and samples becomes important in chemical reactions and analyses performed by mixing a trace reagent and a sample inside a microdevice. This is because chemical reactions and analyses do not proceed as intended when a reagent and a sample are not sent at appropriate timings or in appropriate amounts. Accordingly, there is a need to control parameters such as the flow amount, the flow rate, and the pressure of the fluid being sent.

The centrifugation technique, and the technique to directly enclose air pressure in a channel are two of the methods available to send liquid inside a microdevice. However, both of these techniques involve difficulties in sending liquid in isolation from ambient air, and there is concern that contamination by suspended DNA in air still might occur. It is also difficult with these techniques to control the flow amount and the flow time of fluid.

The present invention is intended to solve the foregoing problems, and an object of the invention is to provide a disposable biochemical cartridge that enables the flow amount of liquids such as reagents to be easily controlled in isolation from ambient air, and a biochemical processing apparatus using such a cartridge.

Solution to Problem

In order to solve the foregoing problems, the present invention uses the configurations set forth in the claims below.

As a specific example, (1) a biochemical cartridge according to the present invention is configured to include a sending chamber that encloses a reagent to be sent, and a receiving chamber for receiving the reagent. The chambers are provided by being sealed inside a cartridge main body, and an elastic body membrane is attached to the bottom surface of the cartridge main body. The membrane is not bonded to a portion that becomes a flow path between the chambers, and a flow path is formed only after the membrane is deformed in the unbonded portion. Membrane deformation also provides a pump function that varies the volume of the flow path with the reciprocal movement of the membrane in response to changes in externally applied pressure.

Specifically, for example, the biochemical cartridge is configured to include a chamber enclosing a liquid specimen, a chamber enclosing a reagent, and a plurality of chambers in which a target biological material is extracted, purified, amplified, denatured, and analyzed in series from a mixture of the liquid specimen and the reagent. The chambers are provided by being sealed in the cartridge main body. The elastic body membrane is attached to the bottom surface of the cartridge main body. The membrane is not bonded to a portion that becomes a flow path between the chambers, and a flow path is formed only after the membrane is deformed in the unbonded portion. Membrane deformation also provides a pump function that varies the volume of the flow path with the reciprocal movement of the membrane in response to changes in externally applied pressure.

As a specific example, (2) a biochemical processing apparatus according to the present invention includes the following constituting elements, in addition to the biochemical processing cartridge. Specifically, the biochemical processing apparatus additionally includes: a cartridge holder that holds the cartridge, and includes an air pressure applying section for applying air pressure to activate the membrane as the pump mechanism; and an air supply and exhaust mechanism that is connected to an air pressure source, and controls the supply and exhaust of the air pressure to and from the cartridge holder.

Advantageous Effects of Invention

In the biochemical cartridge in (1) above, liquids such as reagents and samples can be sent in a non-contact fashion, and can be biochemically processed inside a sealed space to prevent contamination.

In the biochemical processing apparatus in (2) above, the air supply and exhaust mechanism for driving a valve function that operates to open and close a flow opening of each chamber in the cartridge, and the air pressure applying section that activates the flow pump (membrane) of the cartridge are provided on the cartridge holder side to reduce the size and cost of the cartridge.

Other objects, configurations, and effects will be more clearly understood from the descriptions of the embodiment below.

BRIEF DESCRIPTION OF DRAWINGS

FIG. 1 is a block diagram of the units used to solve the problems.
FIG. 2 is a plan view representing a brief overview of a cartridge.
FIG. 3 is a block diagram of an air pressure control system.
FIG. 4 is a diagram representing direction control by a three-way valve in a normal state and an energized state.
FIG. 5 is a cross sectional view of the cartridge at A-A.
FIG. 6 is a cross sectional view of a cartridge holder at A-A.
FIG. 7 is a cross sectional view of the cartridge at A-A set on the cartridge holder.
FIG. 8 is a cross sectional view of a channel at B-B.
FIG. 9 is a diagram representing an example of a channel shape that improves flow accuracy.
FIG. 10 is a diagram representing a series of movements in accordance with the present invention.
FIG. 11 is a diagram representing a series of movements in accordance with the present invention.
FIG. 12 is a diagram representing a series of movements in accordance with the present invention.
FIG. 13 is a diagram representing a series of movements in accordance with the present invention.
FIG. 14 is a diagram representing a series of movements in accordance with the present invention.
FIG. 15 is a diagram representing a series of movements in accordance with the present invention.
FIG. 16 is a diagram representing a series of movements in accordance with the present invention.
FIG. 17 is a diagram representing a series of movements in accordance with the present invention.
FIG. 18 is a diagram representing a series of movements in accordance with the present invention.
FIG. 19 is a diagram representing a series of movements in accordance with the present invention.
FIG. 20 is a diagram representing a series of movements in accordance with the present invention.
FIG. 21 is a cross sectional view of a trace reagent enclosing section.

DESCRIPTION OF EMBODIMENTS

An embodiment of the present invention is described below byway of Example with reference to the accompanying drawings.

FIG. 1 illustrates a biochemical processing apparatus according to Example of the present invention. As an example of nucleic acid extraction and amplification, the biochemical processing apparatus performs a series of processes from extraction to amplification of DNA. The biochemical processing apparatus has three units: A biochemical cartridge 1 that runs the series of processes in a sealed state; a cartridge holder 2 that supports the cartridge 1, and has an air pressure applying section that opens and closes the flow paths of the cartridge 1 to enable a pump operation on the cartridge 1; and an air pressure control system 3 that is connected to an air pump (air pressure source) 30 to control the supply, exhaust, and suction of air pressure in the cartridge holder 2.

Referring to FIG. 2, an example of a brief overview of the cartridge 1 is described first. FIG. 2 is a schematic plan view of the cartridge 1.

The cartridge 1 has a total of four lanes including control lanes 25-a and 25-b used to determine whether the processes are properly run in the cartridge 1, a sample analyzing lane 26 used to analyze a specimen (hereinafter, referred to as "sample") containing a collected biological material, and a reference lane 27 used to provide a reference for analysis.

The cartridge 1 includes a swab enclosing chamber 6 in which a swab 5 that has collected a sample is directly enclosed, reagent enclosing chambers for enclosing various reagents (for example, a solution enclosing chamber 7 that encloses a solution for nucleic acid extraction, amplification reagent enclosing chambers 8-a and 8-b that enclose PCR amplification reagents, and denature reagent enclosing chambers 9 that enclose a reagent used to denature amplified products), branch relay chambers 10 to which a mixture of two amplification reagents is sent by being branched, denature reagent mixing chambers 11 where mixing with a denature reagent takes place, thermostat chambers 12 that regulate and maintain temperature for PCR and denaturation, and capillary junction chambers 13 connected to capillaries to perform electrophoresis after the processes. These chambers are joined to each other with single flow channels 14 and branched flow channels 15. The cartridge 1 also includes trace reagent enclosing sections 16 where trace reagents enclosed in the channels are mixed with liquid upon sending of the liquid. Liquid is allowed to pass through the channels 14 and 15 upon opening of flow openings of corresponding chambers with a valve function (described later), and suction by the air pressure control system 3. A pump function (described later) is used to create such a liquid flow. The channels 14 and 15 described herein admit the passage of a fluid in relevant steps. For the passage of liquid, relevant channels are valved open by using the valve mechanism, whereas the other channels remain closed with the valve function.

In this Example, the swab enclosing chamber 6 also serves as a chamber in which agitation (described later) and extraction take place with a solution introduced from the solution enclosing chamber 7 via the single flow channel 14. The amplification reagent enclosing chambers 8-$a$ and 8-$b$ also serve as chambers, whereby an amplification reagent enclosing chambers 8-$a$ is agitated with another amplification reagent enclosing chambers 8-$b$ via the single flow channel 14. One of the branch relay chambers 10 also serves as a reagent wastechamber to which excess reagents are discarded for the quantification of reagents after PCR. These chambers may be separately provided.

The following describes exemplary procedures of the processes by the cartridge 1. First, the swab 5 with the collected sample is enclosed and sealed in the swab enclosing chamber 6. A solution is then sent to the swab enclosing chamber 6 from the solution enclosing chamber 7, and agitated therein to extract nucleic acids from the sample. Here, the solution is agitated by being moved back and forth in the swab enclosing chamber 6 and the single flow channel 14. The sent solution may be bubbled by sending air. Thereafter, the extract is sent to the solution enclosing chamber 7 in whole amount, and a certain amount is sent to the denature reagent enclosing chamber 9. Meanwhile, the reagent in the amplification reagent enclosing chamber 8-$a$ is sent to the amplification reagent enclosing chamber 8-$b$, and agitated therein in the same fashion. The liquid is then sent to the branch relay chamber 10 through the branched flow channel 15, and then to the denature reagent mixing chamber 11. The liquid sent to the control lanes 25-$a$ and 25-$b$ is accompanied by a trace reagent from the trace reagent enclosing sections 16. On the control lanes 25-$a$ and 25-$b$ and the sample analyzing lane 26, the liquids are agitated in the denature reagent mixing chambers, sent to the thermostat chambers 12 in whole amount, and subjected to PCR in the thermostat chambers 12. After PCR, the whole amount of the PCR solution is sent back to the denature reagent mixing chamber 11, and a certain amount is discarded into the branch relay chamber 10. As a result, only a part of the PCR solution remains in the denature reagent mixing chamber 11. A denature reagent is sent to the denature reagent mixing chamber 11 from the denature reagent enclosing chamber 9, and mixed with the PCR solution in the denature reagent mixing chamber 11. The liquid is then resent to the thermostat chamber 12 for denaturation. Finally, the denatured solution is sent to the capillary junction chamber 13. The capillary junction chamber 13 is connected to a capillary (not illustrated), and capillary electrophoresis is performed for DNA analysis.

Here, a mixture of amplification reagents is channeled into branches in the processes performed in the cartridge 1. By knowing that the liquids sent to different lanes come from the same mixture, it can be certain that different analysis results yielded in different lanes are not due to the degradation or the compositional differences of the reagents enclosed in the cartridge 1. This improves the reliability of analysis results.

In this technique, the solution after PCR is sent back to the denature reagent mixing chamber 11 that has admitted the passage of the liquid before, and the excess solution is discarded into the branch relay chamber 10. The remaining solution is then mixed with the denature reagent. This sending method allows the reagents to be moved back and forth between chambers, and the chambers and the channels that have admitted the passage of liquid can be reused. This enables miniaturizing the cartridge 1, thereby improving the handling of the cartridge 1, and reducing costs.

The structures of the cartridge 1 and the cartridge holder 2 are described below with reference to FIGS. 5 to 9, and FIG. 21.

FIG. 5 is a cross sectional view of the cartridge 1 taken at A-A (see FIG. 2), schematically representing the amplification reagent enclosing chambers 8-$a$ and 8-$b$, and the branch relay chamber 10. The other chambers are formed in the same fashion, and are omitted from the figure.

As shown in FIG. 5, the amplification reagent enclosing chambers 8-$a$ and 8-$b$, and the branch relay chamber 10 are formed in a cartridge main body 50 of the cartridge 1, and a membrane 51 is attached to the bottom surface of the cartridge main body 50. Instead of being attached to the whole bottom surface of the cartridge main body 50, the membrane 51 is attached to only a membrane attaching portion 53, excluding the portions that become the single flow channels 14 and the branched flow channels 15. The portions that become the single flow channels 14 and the branched flow channels 15 do not form grooves that serve as channels in the cartridge main body. Specifically, the cartridge 1 does not have any space that serves as channels joining the chambers, but has the membrane 51 laid on such portions without being bonded. The membrane 51 is pulled under air pressure in portions that become the single flow channels 14 and the branched flow channels 15, and expanded to form a channel. Such a reciprocal movement of the membrane 51 provides a pump function to vary the volume of the flow channel. With the cartridge structure where there is initially no channel, the amounts of air that might otherwise enter the channels of the cartridge 1 can be reduced as much as possible. When channels are initially present in the cartridge 1, the air in the channels will have adverse effect on flow accuracy. For example, any slight applied force on the channels will move the inside air, and the enclosed reagent will trap air when setting the cartridge 1 on the cartridge holder 2. Care also must be taken in handling the cartridge 1. All these problems can be solved with the cartridge structure in which the channels are initially absent.

The chambers have openings 54-$a$ to 54-$d$ that can be sealed with the valve mechanism (described later). Reagents are enclosed in the cartridge beforehand, and a film 52 is attached to the top surface after enclosing the reagents to seal the cartridge 1.

FIG. 21 is a cross sectional view of the trace reagent enclosing section 16 in the cartridge 1. Many of the reagents needed for gene analysis are expensive. The reagent amounts thus need to be reduced to reduce running costs. Reducing the amounts of reagents used requires storing and accurately sending a trace reagent. With a trace reagent enclosed in the channel beforehand as shown in FIG. 21, the trace reagent becomes simultaneously mixed with other reagents being sent in greater amounts. This eliminates the need to handle trace reagents. Further, because the amount of air in the trace reagent enclosed space can be reduced, it is possible to reduce the concentration changes of the reagents due to factors such as condensation.

The cartridge 1 is disposable, and needs to be made of materials that are desirable for mass production. Among the qualities required for the cartridge 1 are heat resistance against PCR reaction, chemical resistance against long storage of the enclosed reagents, and biochemical stability. The cartridge main body 50 is therefore desirably made of polycarbonate resin, polypropylene resin, or polyolefin resin, taking in consideration mass production by resin molding. The membrane 51 is desirably made of silicone rubber or PDMS, which are proven to be useful in the field of biochemistry. A problem with silicone-based materials, however, is that the reagents undergo concentration changes because these materials pass moisture such as during the storage of reagents. Use of less moisture permeable EPDM is thus also possible. The cartridge 1 is fabricated by bonding these materials by chemical bonding, or with the use of an adhesive or a double-sided tape. The film 52 attached to the top surface needs to be a film of low moisture permeability for the storage of reagents. Use of products such as a plate adhesive sheet intended for PCR plates is also desirable because such adhesive sheets provide strong adhesion, and can be attached with a simple procedure.

FIG. 6 is a cross sectional view of the cartridge holder 2 taken at A-A (see FIG. 2), corresponding to the A-A cross sectional view of the cartridge 1 shown in FIG. 5. As an example, the cartridge holder 2 has an air cylinder mechanism that provides the valve function for opening and closing the openings 54-$a$ to 54-$d$ of the amplification reagent enclosing chambers 8-$a$ and 8-$b$ and the branch relay chamber 10 shown in FIG. 5, and an air pressure supply and exhaust mechanism that provides the pump function based on the reciprocal movement of the membrane 51. Though not shown in FIG. 5, the air cylinder mechanism, and the air pressure supply and exhaust mechanism are also provided for the other chambers. The following describes the air cylinder mechanism, the air pressure supply and exhaust mechanism, and the configuration of the cartridge holder 2.

The cartridge holder 2 has a three-layer structure including a holder base 60, a holder top 61, and a holder middle plate 62, which are fixed with gaskets 63-$a$ and 63-$b$ interposed in between. Pin-shaped plungers 64-$a$ to 64-$d$ that operate as the air cylinder mechanism upon being driven by air pressure changes are installed inside the cartridge holder 2, with corresponding packings 65-$a$ and 65-$b$ fitted in place. Also provided in the cartridge holder 2 are uplifting air pressure ports 66-$a$ to 66-$d$ through which air pressure is introduced to lift up the plungers 64-$a$ to 64-$d$, and downlifting air pressure ports 67-$a$ to 67-$d$ for lifting down the plungers 64-$a$ to 64-$d$. Uplifting and downlifting of the plungers 64-$a$ to 64-$d$ cause a part of the membrane 51 to undergo elastic deformation, and open and close the openings 54-$a$ to 54-$d$. The air cylinder mechanism thus provides the valve function. The holder top 61 has grooves that become channels. The single flow channel 14 and the branched flow channel 15 shown in FIG. 6 are formed upon deforming the membrane 51. The same is the case for other channels. As described above, the channels are formed only after the membrane 51 is pulled and deformed by suction, and channel depressurization ports 69-$a$ and 69-$b$ are provided for the pump function. The membrane needs to be brought into contact with the holder top 61 and the cartridge main body 50 to improve flow accuracy, and channel pressurization ports 68-$a$ and 68-$b$ are provided for this purpose. In this way, the membrane 51 can deform not only by virtue of its elastic force but by being forcibly deformed. This enables controlling the deformation amount, and improving flow accuracy. At the edges of the channels are provided channel projections 70 that prevent leakage of air pressure. By isolating the channels from one another, the channel projections 70 allow air pressure to be applied only to a channel that needs to be activated.

The holder base 60, the holder top 61, and the holder middle plate 62 are desirably made of acrylic resin. The complexity of the air pressure channels increases as the number of flow locations increases. By being bondable, acrylic resins can accommodate complex channels, and can make the system more compact. An increase in the number of flow locations is accompanied by corresponding increase in plunger numbers. Costs can be reduced by molding the plungers with a rigid resin such as PPS resin. However, care must be taken that the parting lines created by molding do not cause air leakage. The packings are selected from materials designed for air pressure reciprocation, and a grease is applied to the sliding portions. The grease is also selected from products designed for air pressure driving. In this way, the slide friction of the plungers can be reduced.

FIG. 7 is an A-A cross sectional view of the cartridge 1 (see FIG. 2) set on the cartridge holder 2. With the cartridge 1 set on the cartridge holder 2, the openings 54-$a$ to 54-$d$ of the chambers in the cartridge 1 are aligned with the plungers 64-$a$ to 64-$d$ of the cartridge holder 2. In this way, the openings 54-$a$ to 54-$d$ of the chambers can be opened and closed by driving the plungers 64-$a$ to 64-$d$ with the air cylinder mechanism.

FIG. 8 is a cross sectional view of the cartridge 1 set on the cartridge holder 2, taken at B-B of FIG. 7. The holder top 61 has the channel projections 70 at the channel edges, and the cartridge main body 50 has channel grooves 71 carved therein to fit the channel projections. The cartridge 1 and the cartridge holder 2 are structured so that channels are created upon fitting and setting the channel projections 70 in the channel grooves 71. When the mating of the channel grooves 71 and the channel projections 70 is not provided, the regions of the cartridge main body 50 where the membrane 51 is not attached serves as the channels directly. Accurate control of the dimensions in which the membrane 51 is attached to the cartridge main body 50 is difficult to achieve in cartridge production. The dimensional accuracy of the channels can be improved by creating channels in regions bordered by the channel projections 70. In the sending method described herein, the amount of liquid sent is determined by the channel volume, and improving the dimensional accuracy of the channels directly leads to improved flow accuracy. It is also possible with this structure to prevent the channels from being contacted by the solvent, the adhesive, the double-sided tape, or other such materials used to bond the cartridge main body 50 and the membrane 51. These materials are often biochemically unstable, and have the risk of generating an out-gas. Reliability can thus improve by preventing such materials from being exposed to the channels. In this structure, a slight tension is created in the membrane 51 upon setting the cartridge 1 on the cartridge holder 2. This prevents buckling of the membrane 51, and enables the membrane 51 to smoothly contact the cartridge main body 50, and improve flow accuracy.

In order to create an accurate flow, the membrane 51 needs to smoothly contact the groove carved in the holder top 61 to create a channel. Such a smooth contact can be achieved by creating a depth difference in the channel as in the single flow channel 14-$a$ and the branched flow channel 15-$a$ shown in FIG. 9. When a fluid is drawn in the channel in the absence of such a depth difference, there is a possibility that the air pressure port being vacuumed becomes closed before the membrane 51 contacts the whole groove that becomes a channel. On the other hand, with a depth difference created in the channel as shown in FIG. 9, the membrane 51 is able to smoothly contact the channel, and the flow accuracy can be improved further. The same effect can be obtained by creating a difference in channel width. Note, however, that this is applicable only when liquid is sent in one direction, because accuracy suffers when liquid is sent in reverse direction in the same channel.

As described above, liquid is sent by activating the pump function and the valve function with the cartridge 1 set on the cartridge holder 2 connected to the air pressure control system 3. However, sending of liquid does not take place without the air pressure control performed by the air pressure control system 3. In a normal state, all the air pressure ports of the cartridge holder 2 are open to the atmosphere.

FIG. 3 represents the configuration of the air pressure control system 3. An air pump 30 as the driving source of air pressure is provided for suction and discharge of air. Air is discharged into a pipe, and coupled to a branched pipe 35 through a filter 31 and a pressure adjusting valve 32. One end of the branched pipe 35 is connected to an open atmosphere two-way valve 33, and opened to the atmosphere at a silencer 34-b. The other end is connected to a pressurizing three-way valve manifold 38-a through a pressurization pipe two-way valve 36. The open atmosphere two-way valve 33 and the pressurization pipe two-way valve 36 are normally closed, and the channels are closed in a normal state, and become open only upon being energized. Inside the pressurizing three-way valve manifold 38-a are installed pressurizing three-way valves 39-a, which are connected to the cartridge holder 2 via pressurizing speed controllers 40-a. A silencer 34-a is installed at the open atmosphere portion of the pressurizing three-way valve manifold 38-a. The suction side of the air pump 30 is connected to a depressurization pipe three-way valve 37 via a pipe. One end of the depressurization pipe three-way valve 37 is an open atmosphere portion 41, whereas the other end is connected to a depressurizing three-way valve manifold 38-b. Inside the depressurizing three-way valve manifold 38-b are installed depressurizing three-way valves 39-b, which are connected to the cartridge holder 2 via depressurizing speed controllers 40-b. A depressurization open atmosphere speed controller 40-c, and a silencer 34-c are installed at the open atmosphere portion of the depressurizing three-way valve manifold 38-b.

Dust and particles contained in air are removed as the discharged air from the air pump 30 passes through the filter 31. This prevents entry of foreign objects into the pipe. The pressure adjusting valve 32 enables creating an appropriate pressure by adjusting the air pressure supplied to the cartridge holder 2. With the pressurizing three-way valves 39-a and the depressurizing three-way valves 39-b installed on their respective manifolds, connection of the pipes can be gathered at one location. Because the pipe can be connected at one location even when there is any increase in number of three-way valves, the system can be provided in a more compact design. The speed controllers are connected to each of the pipes connected to the cartridge holder 2 to control air flow amounts. Because sending of liquid is performed with air pressure, the flow amount of air pressure is closely related to the flow amount of liquid, and this relationship becomes very important. With the speed controller also installed at the open atmosphere portion of the depressurizing three-way valve manifold 38-b, the negative pressure applied to the membrane 51 can be slowly brought back to the atmospheric pressure. This also can be used to control the flow amount of liquid. The silencer provided at the open atmosphere portion reduces the exhaust noise.

FIG. 4 represents the direction control by the three-way valves provided in the configuration of the air pressure control system 3. In this piping system, direction control is different for the three-way valves installed in the manifolds, and the three-way valve not installed in the manifolds.

The direction control by the three-way valves installed in the manifolds is described first. Each of the three-way valves 39 installed in the three-way valve manifold 38 is switchable between an air pressure channel 45 joining the IN side to the cartridge holder 2 side, and an air pressure channel 46 joining the cartridge holder 2 side to the OUT side. The three-way valve 39 is normally closed, so that the air pressure channel 45 is closed, and air pressure channel 46 is open in a normal state. Here, the incoming air from the IN side is coupled to the three-way valve manifold 38. However, with the air pressure channel 45 closed, no air pressure is applied to the cartridge holder 2 side. On the other hand, the air pressure channel 46 is open, and the channel joining the cartridge holder 2 side and the OUT side is open to the atmosphere. Energizing the three-way valve 39 opens the air pressure channel 45, and the air pressure channel 46 is closed. Here, the air from the IN side is coupled to the three-way valve manifold 38, and, with the air pressure channel 45 open, can exert its pressure on the cartridge holder 2 side. Because the pipe is connected to the cartridge holder 2 side via the three-way valves 39, the air pressure can be applied to only the three-way valves that are energized. This makes it possible to apply air pressure to only the desired channels. The direction control described above is the same for the pressurizing three-way valve manifold 38-a and the depressurizing three-way valve manifold 38-b.

The direction control by the depressurization pipe three-way valve 37 is described below. The depressurization pipe three-way valve 37 is switchable between an air pressure channel 47 joining the depressurizing three-way valve manifold 38-b side to the air pump 30, and an air pressure channel 48 joining the open atmosphere portion 41 to the air pump 30. The depressurization pipe three-way valve is normally closed, so that the air pressure channel 47 is closed, and the air pressure channel 48 is open in a normal state, causing the air pump 30 to draw in air through the open atmosphere portion 41. Energizing the depressurization pipe three-way valve 37 opens the air pressure channel 47, and closes the air pressure channel 48, causing the air pump 30 to draw in air through the depressurizing three-way valve manifold 38-b.

The following describes how liquid is flown in the cartridge 1 of the foregoing configuration, with reference to FIGS. 10 to 20. The liquid flow described below is from the amplification reagent enclosing chamber 8-a to the amplification reagent enclosing chamber 8-b, and to the branch relay chamber 10.

In preparation to send liquid, the air pump 30 is activated before connecting the cartridge holder 2 and the air pressure control system 3. The depressurization pipe three-way valve 37 is joined to the open atmosphere portion 41, and the open atmosphere two-way valve 33 and the pressurization pipe two-way valve 36 are normally closed, causing the pressure from the air pump 30 to increase between these two-way valves. Here, the pressure adjusting valve 32 is used to appropriately adjust the pressure. Thereafter, the pressurization pipe two-way valve 36 is energized to energize the pressurizing three-way valves 39-a. This causes air to be sent to the pipes connected to the cartridge holder 2. In this state, the pressurization pipe speed controllers 40-a adjust the flow amount in each pipe connected to the cartridge holder 2. The flow amount on the depressurization pipe side is also adjusted in the same manner. After the air pressure and flow amount adjustments, the air pump 30 is turned off, and the residual pressure inside the pipes is exhausted. The air pressure control system 3 is then connected to the cartridge holder 2. The pipes from the depressurizing three-way valves 39-b are connected to only the channel depressurization ports 69-*a* and 69-*b* of the cartridge holder 2, whereas the pipes from the pressurizing three-way valves 39-*a* are connected to the other air pressure ports. The cartridge 1 is set on the cartridge holder 2 after connecting the pipes.

The following describes the air pressure control method, and the accompanying plunger and fluid movements.

(1) The air pump 30 is activated. This causes air to be drawn in through the open atmosphere portion 41 of the depressurization pipe three-way valve 37, and creates an increased pressure inside the pipe from the air pump 30 to the open atmosphere two-way valve 33 and the pressurization pipe two-way valve 36.

(2) The pressurization pipe two-way valve 36 is energized. This opens the pressurization pipe two-way valve 36, and air pressure is applied to the pressurizing three-way valve manifold 38-*a*. Because the pressurizing three-way valves 39-*a* are not energized, the air pressure does not propagates to the cartridge holder 2.

(3) The pressurizing three-way valves 39-*a* connected to the downlifting air pressure ports 67-*a* and 67-*b* connected to the cartridge holder 2 are energized. This lifts down the plungers 64-*a* to 64-*d* installed in the cartridge holder 2 as shown in FIG. 10. This operation is performed to ensure the downlifting of the plungers 64-*a* to 64-*d* in the initial state.

(4) The pressurizing three-way valve 39-*a* connected to the uplifting air pressure port 66-*b* is energized, and the pressurizing three-way valve 39-*a* connected to the downlifting air pressure port 67-*b* is deenergized. This lifts up the plunger 64-*b* as shown in FIG. 11, and seals the opening 54-*b*.

(5) The pressurization pipe two-way valve 36 is deenergized. Because the pressurization pipe two-way valve 36 is normally closed, the pipe from the pressurization pipe two-way valve 36 is closed. The pressurizing three-way valve manifold 38-*a* thus remains under increased pressure.

(6) The open atmosphere two-way valve 33 is energized, and the depressurization pipe three-way valve 37 is energized. This causes air to be drawn in from the depressurizing three-way valve manifold 38-*b*, and opens the open atmosphere two-way valve 33, creating a negative pressure inside the pipe from the air pump 30 to the depressurization pipe three-way valve manifold 38-*b*.

(7) The depressurizing three-way valve 39-*b* connected to the channel depressurization port 69-*a* is energized. This creates a negative pressure in the single flow channel 14 portion as shown in FIG. 12, and the membrane 51 contacts the holder top 61. Here, the opening 54-*a* is open, and the opening 54-*b* is sealed. The reagent is thus sent into the thus created single flow channel 14 from the amplification reagent enclosing chamber 8-*a*.

(8) The depressurization pipe three-way valve 37 is deenergized. This maintains the negative pressure in the pipe from the depressurization pipe three-way valve 37 to the depressurizing three-way valve manifold 38-*b*.

(9) The open atmosphere two-way valve 33 is deenergized. This recreates an increased pressure inside the pipe from the air pump 30 to the open atmosphere two-way valve 33 and the pressurization pipe two-way valve 36.

(10) The pressurization pipe two-way valve 36 is energized. This recreates an increased pressure inside the pipe from the air pump 30 to the pressurizing three-way valve manifold 38-*a*.

(11) The pressurizing three-way valve 39-*a* connected to the uplifting air pressure port 66-*a* is energized, and the pressurizing three-way valve 39-*a* connected to the downlifting air pressure port 67-*a* is deenergized. This lifts up the plunger 64-*a* as shown in FIG. 13, and seals the opening 54-*a*.

(12) The pressurizing three-way valve 39-*a* connected to the uplifting air pressure port 66-*b* is deenergized, and the pressurizing three-way valve 39-*a* connected to the downlifting air pressure port 67-*b* is energized. This lifts down the plunger 64-*b* as shown in FIG. 14, and opens the opening 54-*b*.

(13) The depressurizing three-way valve 39-*b* connected to the channel depressurization port 69-*a* is deenergized, and the pressurizing three-way valve 39-*a* connected to the channel pressurization port 68-*a* is energized. This creates an increased pressure in the single flow channel 14 portion as shown in FIG. 15, and the membrane 51 contacts the cartridge main body 50. Here, the opening 54-*a* is sealed, and the opening 54-*b* is open. The reagent in the single flow channel 14 is thus sent into the amplification reagent enclosing chamber 8-*b*.

(14) The pressurizing three-way valve 39-*a* connected to the uplifting air pressure port 66-*d* is energized, and the pressurizing three-way valve 39-*a* connected to the downlifting air pressure port 67-*d* is deenergized. This lifts up the plunger 64-*d* as shown in FIG. 16, and seals the opening 54-*d*.

(15) The pressurization pipe two-way valve 36 is deenergized. Because the pressurization pipe two-way valve 36 is normally closed, the pipe from the pressurization pipe two-way valve 36 becomes closed. The pressurizing three-way valve manifold 38-*a* thus remains under increased pressure.

(16) The open atmosphere two-way valve 33 is energized, and the depressurization pipe three-way valve 37 is energized. This causes air to be drawn in from the depressurizing three-way valve manifold 38-*b*, and opens the open atmosphere two-way valve 33, creating a negative pressure inside the pipe from the air pump 30 to the depressurization pipe three-way valve manifold 38-*b*.

(17) The depressurizing three-way valve 39-*b* connected to the channel depressurization port 69-*b* is energized. This creates a negative pressure in the branched flow channel 15 portion as shown in FIG. 17, and the membrane 51 contacts the holder top 61. Here, the opening 54-*c* is open, and the opening 54-*d* is sealed. The reagent is thus sent into the thus created branched flow channel 15 from the amplification reagent enclosing chamber 8-*b*.

(18) The depressurizing three-way valve 39-*b* connected to the channel depressurization port 69-*b* is deenergized. This causes the branched flow channel 15 to return to its original shape under the elastic force of the membrane 51. Here, the opening 54-*c* is open, and the opening 54-*d* is sealed. The reagent thus returns into the amplification reagent enclosing chamber 8-*b*.

(19) The operations of (17) and (18) are repeated several times. This is to agitate the amplification reagents. After agitation, only the operation of (17) is performed to form the branched flow channel 15 again as shown in FIG. 17, and send the reagents.

(20) The depressurization pipe three-way valve 37 is deenergized. This maintains the negative pressure inside the pipe from the depressurization pipe three-way valve 37 to the depressurizing three-way valve manifold 38-*b*.

(21) The open atmosphere two-way valve 33 is deenergized. This recreates an increased pressure inside the pipe from the air pump 30 to the open atmosphere two-way valve 33 and the pressurization pipe two-way valve 36.

(22) The pressurization pipe two-way valve 36 is energized. This recreates an increased pressure inside the pipe from the air pump 30 to the pressurizing three-way valve manifold 38-*a*.

(23) The pressurizing three-way valve 39-*a* connected to the uplifting air pressure port 66-*c* is energized, and the pressurizing three-way valve 39-*a* connected to the downlifting air pressure port 67-*c* is deenergized. This lifts up the plunger 64-*c* as shown in FIG. 18, and seals the opening 54-*c*.

(24) The pressurizing three-way valve 39-*a* connected to the uplifting air pressure port 66-*d* is deenergized, and the pressurizing three-way valve 39-*a* connected to the downlifting air pressure port 67-*d* is energized. This lifts down the plunger 64-*d* as shown in FIG. 19, and opens the opening 54-*d*.

(25) The depressurizing three-way valve 39-*b* connected to the channel depressurization port 69-*c* is deenergized, and the pressurizing three-way valve 39-*a* connected to the channel pressurization port 68-*c* is energized. This creates an increased pressure in the branched flow channel 15 portion as shown in FIG. 20, and the membrane 51 contacts the cartridge main body 50. Here, the opening 54-*c* is sealed, and the opening 54-*d* is open. The reagent in the branched flow channel 15 is thus sent into the branch relay chamber 10.

By performing these operations for the relevant chambers in the cartridge 1, a reagent from any chamber can be sent to any location at any timing. The amount of liquid sent may be determined by the number of times the membrane 51 is deformed. Because any desired chambers can be sealed for extraction, reaction, and agitation, the fluid can be stably controlled. This enables liquid to be stably sent without contacting the fluid inside the sealed cartridge 1 in various processes.

There are a number of reagents that are necessary for the pretreatment of gene analysis, as described in FIG. 2. The present liquid sending system can accommodate larger numbers of reagents simply with the use of the air pump 30 configured as the driving source into the air pressure control system 3. Any increase in the number of cartridges 1 in the device also can be accommodated by increasing the number of interconnections between the three-way valves and the pipes in the system, without adding a driving source. The system can thus be said as being versatile. The cost and size of the device also can be reduced.

The valve function is provided by the plungers installed on the cartridge holder 2 side, and the structure of the cartridge 1 itself can be simplified. Because the cartridge 1 is disposable, reducing the unit price of the cartridge 1 itself directly leads to reduction of running costs. The valve function may be provided inside the cartridge 1. Liquid also may be sent by deforming the channel under air pressure with the use of a check valve installed inside the cartridge 1 in a position sealed with a pin. Such check valves may be installed by using, for example, a method that uses a commercially available check valve, a method that uses a rubber ball to provide a check valve function, or a method in which three-dimensionally shaped membranes 51 are used and bonded to each other. This simplifies the structure on the cartridge holder 2 side, and the device cost can be reduced. However, the installation of the check valve in the cartridge 1 adds to the unit price of the cartridge 1 itself.

By being applied to the currently available methods that use air pressure to send liquid, the present system enables sending liquid while enabling the fluid to be easily controlled at the same time. Instead of deforming the channels under air pressure, the chamber itself may be deformed under air pressure to send liquid. Deformation may be achieved not by air pressure but by using objects such as rollers. Sending of liquid under the fluid control is also possible in a method that directly applies air pressure to the channels. However, in order to directly apply air pressure to the channels, contamination with suspended DNA in air needs to be prevented. This necessitates the provision of a filter, and increases the cost of the cartridge 1.

While there have been described a certain embodiment of the invention, it will be understood by a skilled person that the invention is not limited to the foregoing descriptions, and various modifications may be made thereto within the scope of the invention set forth in the claims below. An embodiment based on combinations of the foregoing Examples as may be appropriately made also falls within the scope of the present invention. The foregoing Examples described the case where the biological materials applied to the invention are nucleic acids, particularly DNA. However, the invention is not limited to this, and is applicable to a whole range of biological materials, including, for example, RNAs, proteins, polysaccharides, and microorganisms.

REFERENCE SIGNS LIST

1 Cartridge
2 Cartridge holder
3 Air pressure control system
5 Swab
6 Swab enclosing chamber
7 Solution enclosing chamber
8 Amplification reagent enclosing chamber
9 Denature reagent enclosing chamber
10 Branch relay chamber
11 Denature reagent mixing chamber
12 Thermostat chamber
13 Capillary junction chamber
14 Single flow channel
15 Branched flow channel
16 Trace reagent enclosing section
25 Control lane
26 Sample analyzing lane
27 Reference lane
30 Air pump
31 Filter
32 Pressure adjusting valve
33 Open atmosphere two-way valve
34 Silencer
35 Branched pipe
36 Pressurization pipe two-way valve
37 Depressurization pipe three-way valve
38 Three-way valve manifold
39 Three-way valve
40 Speed controller
41 Open atmosphere portion
45, 46, 47, 48 Air pressure channel
50 Cartridge main body
51 Membrane
52 Film
53 Membrane attaching portion
54 Opening
60 Holder base
61 Holder top
62 Holder middle plate
63 Gasket
64 Plunger
65 Packing 66 Uplifting air pressure port
67 Downlifting air pressure port
68 Channel pressurization port
69 Channel depressurization port
70 Channel projection
71 Channel groove

The invention claimed is:

1. A cartridge for sending a liquid inside a sealed space, the cartridge comprising:
   a cartridge main body having a top surface and a bottom surface substantially in one plane;
   a plurality of chambers internally provided in the cartridge main body that accept the liquid, including a first chamber having a first opening, a second chamber having a second opening and a third opening, and a third chamber having a fourth opening; and
   an elastic body having substantially planar top and bottom surfaces wherein one of the surfaces of the elastic body is attached to only first portions of the bottom surface of the cartridge main body among the first portions and second portions of the bottom surface of the cartridge main body,
   wherein the elastic body undergoes deformation with changes in externally applied pressure,
   wherein the elastic body is configured to close the bottom surface side of the plurality of chambers,
   wherein a part of the second portions of the bottom surface of the cartridge main body is between the first opening of the first chamber and the second opening of the second chamber and another part of the second portions of the bottom surface of the cartridge main body is between the third opening of the second chamber and the fourth opening of the third chamber,
   wherein the elastic body only deforms away from the substantially planar bottom surface of the cartridge main body at the second portions of the bottom surface of the cartridge main body wherein a flow channel is formed after the elastic body is deformed,
   wherein in a state without externally applied pressure causing deformation of the elastic body, substantially an entirety of the one surface of the elastic body contacts the bottom surface of the cartridge main body in the one plane,
   wherein at least the first chamber and the second chamber initially hold a reagent, and
   wherein a film is attached to the top surface of the cartridge main body covering each of the first chamber, the second chamber, and the third chamber.

2. A biochemical cartridge system comprising the cartridge of claim 1, and a cartridge holder on which the cartridge is set,
   wherein the cartridge holder has a channel shape formed therein, and the channel is formed in conformity with the channel shape by the deformation of the elastic body.

3. The biochemical cartridge system according to claim 2, wherein the channel has at least one of a height and a width that allows the elastic body to contact the channel shape by the deformation of the elastic body.

4. A biochemical cartridge system comprising the cartridge of claim 1, and a cartridge holder on which the cartridge is set,
   wherein each of the first opening, second opening, third opening and fourth opening are respectively aligned over a first plunger, a second plunger, a third plunger, and a fourth plunger of the cartridge holder.

5. The cartridge according to claim 1, further comprising:
   channel grooves are disposed within at least one of the second portions of the bottom surface of the cartridge main body.

6. The cartridge according to claim 1, further comprising:
   a first channel, a second channel, a third channel, and a fourth channel disposed in the cartridge main body in respective communication with the first opening, the second opening, the third opening, and the fourth opening,
   wherein the each of the first channel, the second channel, the third channel, and the fourth channel extend downward from the chambers to the respective first opening, the second opening, the third opening, and the fourth opening.

* * * * *